(12) United States Patent
Elisseeff

(10) Patent No.: US 8,268,950 B2
(45) Date of Patent: Sep. 18, 2012

(54) GLUCOSAMINE MATERIALS

(75) Inventor: Jennifer H. Elisseeff, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 12/368,636

(22) Filed: Feb. 10, 2009

(65) Prior Publication Data

US 2010/0010187 A1  Jan. 14, 2010

Related U.S. Application Data

(63) Continuation of application No. 11/816,600, filed as application No. PCT/US2006/005748 on Feb. 17, 2006, now abandoned.

(60) Provisional application No. 60/654,151, filed on Feb. 18, 2005.

(51) Int. Cl.
   *C08L 5/08* (2006.01)

(52) U.S. Cl. ......... 527/313; 536/55.2; 530/395

(58) Field of Classification Search ......... 527/313; 536/55.2; 530/395; 525/54.2, 54.21, 54.22, 525/54.23, 54.24; 514/54, 62
See application file for complete search history.

(56) References Cited

U.S. PATENT DOCUMENTS

| | | | | |
|---|---|---|---|---|
| 4,365,050 A * | 12/1982 | Ivani | ............ | 527/312 |
| 5,470,911 A | 11/1995 | Rhee et al. | | |
| 5,510,418 A * | 4/1996 | Rhee et al. | ............ | 525/54.2 |
| 2005/0147679 A1* | 7/2005 | Petito et al. | ............ | 424/484 |
| 2005/0260181 A1* | 11/2005 | Girsh | ............ | 424/93.45 |
| 2007/0098675 A1 | 5/2007 | Elisseeff et al. | | |
| 2009/0047740 A1 | 2/2009 | Elisseeff et al. | | |
| 2009/0076606 A1 | 3/2009 | Huerta et al. | | |
| 2009/0324722 A1 | 12/2009 | Elisseeff | | |
| 2010/0003329 A1 | 1/2010 | Elisseeff | | |

OTHER PUBLICATIONS

Kim, K. S., et al. "Synthesis of polymeric drugs containing D-glucosamine as a spacer", Korea Polymer Journal, vol. 4, No. 1, pp. 16-22, 1996.*
International Search Report mailed Jul. 13, 2006, for corresponding PCT Application No. PCT/US06/05748.
Written Opinion mailed Jul. 13, 2006, for corresponding PCT Application No. PCT/US06/05748.
Bryant SJ, Anseth KS. Hydrogel properties influence ECM production . . . J Biomed Mater Res 2002;59:63-72.
Kolm V, Sauer U, Olgemooller B, Schleicher ED. High glucose-induced TGF-beta 1 regulates mesangial production of heparan sulfate proteoglycan. Am J Physiol 1996;270:F812-21.
Wolf G, Sharma K, Chen Y, Ericksen M, Ziyadeh FN. High glucose-induced proliferation in mesangial cells is reversed by autocrine TGF-beta. Kidney Int 1992; 42:647-56.
Terry DE, Rees-Milton K, Smith P, Carran J, Pezeshki P, Woods C, et al. N-acylation of glucosamine modulates chondrocyte growth, proteoglycan synthesis, and gene expression. J Rheumatol 2005; 32:1775-86.
Kim JJ, Conrad HE. Effect of D-glucosamine concentration on the kinetics of mucopolysaccharide biosynthesis in cultured chick embryo vertebral cartilage. J Bioi Chem 1974;249:3091-7.

(Continued)

*Primary Examiner* — James J Seidleck
*Assistant Examiner* — S. Camilla Pourbohloul
(74) *Attorney, Agent, or Firm* — Johns Hopkins Technology Transfer

(57) ABSTRACT

Polymers comprising glucosamine (GlcN) are used to make medical devices. Examples include polyGlcN and carrier molecules containing multiple GlcN residues.

2 Claims, 6 Drawing Sheets

OTHER PUBLICATIONS

Bekesi JG, Bekesi E, Winzler RJ. Inhibitory effect of D-glucosamine and other sugars on the biosynthesis of protein, ribonucleic acid, and deoxyribonucleic acid in normal and neoplastic tissues. J Biol Chem 1969;244:3766-72.

Chan PS, Caron JP, Rosa GJ, Orth MW. Glucosamine and chondroitin sulfate regulate gene expression and synthesis of nitric oxide and prostaglandin E(2) in articular cartilage explants. Osteoarthritis Cartilage 2005;13:387-94.

Kolm-Litty V, Sauer U, Nerlich A, Lehmann R, Schleicher ED. High glucose-induced transforming growth factor β1 production is mediated by the hexosamine pathway in porcine glomerular mesangial cells. J Clin Invest 1998;101:160-9.

Singh LP, Green K, Alexander M, Bassly S, Crook ED. Hexosamines and TGF-b1 use similar signaling pathways to mediate matrix protein synthesis in mesangial cells. Am J Physiol Renal Physiol 2004;286: F409-16.

Grimaud E, Heymann O, Redini F. Recent advances in TGF-beta effects chondrocyte metabolism. Potential therapeutic roles of TGF beta in cartilage disorders. Cytokine Growth Factor Rev 2002;13: 241-57.

Qiao B, Padilla SR, Benya PD. Transforming growth factor (TGF)-beta-activated kinase 1 mimics and mediates TGF-beta-induced stimulation of type II collagen synthesis in chondrocytes independent of Col2a1 transcription and Smad3 signaling. J Biol Chem 2005;280:17562-71.

Yang X, Chen L, Xu X, Li C, Huang C, Deng CX. TGFb/Smad3 signals repress chondrocyte hypertrophic differentiation and are required for maintaining articular cartilage. J Cell Biol 2001;153:35-46.

Sporn MB, Roberts AB. TGF-β: problems and prospects. Cell Regul 1990;1:875-82.

Darling EM, Athanasiou KA. Biomechanical strategies for articular cartilage regeneration. Ann Biomed Eng. Oct. 2003; 31(9)1 114-24.

Hunter CJ, Mouw JK, Levenston ME. Dynamic compression of chondrocyte-seeded fibrin gels: effects on matrix accumulation and mechanical stiffness. Osteoarthritis Cartilage. Feb. 2004;12(2):117-30.

Steadman JR, Rodkey WG, Rodrigo JJ. Microfracture: surgical technique and rehabilitation to treat chondral defects. Clin Orthop. Oct. 2001;(391 Suppl):S362-9. Review.

Buckwalter JA, Mankin HJ. Articular cartilage: part II-degeneration and osteoarthrosis, repair, regeneration and transplantation. J Bone Joint Surg Am. 79A:612-632, 1997.

Shapiro F, Koide S, Glimcher MJ: Cell origin and differentiation in the repair of full thickness defects of articular cartilage. J Bone Joint Surg. 75A:532-553,1993.

Kim HK, Moran ME, Salter RB. The potential for regeneration of articular cartilage in defects created by chondral shaving and subchondral abrasions. J Bone Joint Surg Am. 73:1301-15, 1991.

Wirth CJ, Rudert M. Techniques of cartilage growth enhancement: a review of the literature. Arthroscopy: The Journal of Arthroscopic and Related Surgery. 12:300-308, 1996.

Nathan S, Das De S, Thambyah a, Fen C, Goh J, Lee EH. Cell-based therapy in the repair of osteochondral defects: a novel use for adipose tissue. Tissue Eng. Aug. 2003;9(4):733-44.

Rubak JM. Reconstruction of articular cartilage defects with free periosteal grafts: an experimental study. Acta Orthop Scand. 53:175-180, 1982.

Bouwmeester PS, Kuijer R, Homminga GN, Bulstra SK, Geesink RG. A retrospective analysis of two independent prospective cartilage repair studies: autogenous perichondrial grafting versus subchondral drilling 10 years postsurgery. J Orthop Res. Mar. 2002;20(2):267-73.

Henderson 1, Tuy B, Oakes B. Reoperation after autologous chondrocyte implantation. Indications and findings. J Bone Joint Surg Br. Mar. 2004;86(2):205-11.

Mummert, M. E., M. Mohamadzadeh, et al. (2000). "Development of a peptide inhibitor of hyaluronanmediated leukocyte trafficking." J Exp Med 192(6): 769-79.

Zmolik, J. M. And M. E. Mummert (2005). "Pep 1 as a novel probe for the in situ detection of hyaluronan." J Histochem Cytochem 53(6): 745-51.

Goa, K. L. And P. Benfield (1994). "Hyaluronic acid. A review of its pharmacology and use as a surgical aid in ophthalmology, and its therapeutic potential in joint disease and wound healing." Drugs 47(3): 536-66.

Lee HJ, Lee JS, Chansakul T, Yu C, Elisseeff JH, Yu 8M: Collagen mimetic peptide-conjugated photopolymerizable peg hydrogel. Biomaterials 2006;27:5268-5276.

Williams CG, Kim TK, Taboas A, Malik A, Manson P, Elisseeff J: In vitro chondrogenesis of bone marrow-derived mesenchymal stem cells in a photopolymerizing hydrogel. Tissue Eng 2003;9:679-688.

Livak KJ, 8chmittgen TD: Analysis of relative gene expression data using real-time quantitative pcr and the 2(-delta delta c(t)) method. Methods 2001;25:402-408.

Steinleitner et al., Obstetrics & Gynecology, 77:48-52 (1991).

Campbell, C., et al., "Targeting pro-invasive oncogenes with short chain fatty acid-hexosamine...", J. Med. Chem. (2008), 51, 8135-8147.

Elmouelhi, N., et al., "The Hexosamine template...", J. Med. Chem., (2009) 52(8); 2515-2530.

Mengshol, J., et al., "IL-1 induces collagenase-3 (MMP-13) promoter activity...", Nucleic Acids Research, 2001, vol. 29, No. 21, 4361-4372.

Sun, SC., et al., "NF-KB controls expression of Inhibitor...", Science vol. 259; Mar. 26, 1993, 1912-1915.

Greene et al., Protective Groups in Organic Synthesis 2nd ed., Wiley, New York, (1991).

Proctor et al., Tetra. Lett. 47(29) 5151-5154, 2006.

Reyes et al., Invest. Ophthai. Vis. Sci. 46(4)1247 (2005).

Lee, J. et al., "Effects of the controlled-release of TGF-beta1 from chitosan microspheres...", Biomaterials (2004) vol. 25, pp. 4163-4173.

Hekmatara, T. et al., "Thermoanalytical study of microspheres...", J. Therm. Anal. Calorim. (2006) vol. 86, pp. 287-290.

Young A., et al., "Regional assessment of articular cartilage gene expression and small proteoglycan metabolism in an animal model of osteoarthritis", Arthritis Res Ther 2005;7:R852-61.

McAlindon T., et al., "Glucosamine and chondroitin for treatment of osteoarthritis: a systematic quality assessment and metaanalysis", JAMA 2000;283:1469-75.

Poolsup N., et al., "Glucosamine long-term treatment and the progression of knee osteoarthritis: systematic review of randomized controlled trials", Ann Pharmacother 2005;39:1080-7.

Muller-Fassbender H., et al., "Glucosamine sulfate compared to ibuprofen in osteoarthritis of the knee", Osteoarthritis Cartilage, 1994;2:61-9.

Matteson A., et al., "Glucosamine: a review of its use in the management of osteoarthritis", Drugs Aging 2003;20:1041-60.

Richy F., et al., "Structural and symptomatic efficacy of glucosamine and chondroitin in knee osteoarthritis: a comprehensive meta-analysis", Arch Intern Med, 2003;163:1514-22.

Reginster J., et al., "Long-term effects of glucosamine sulphate on osteoarthritis progression: a randomised, placebo-controlled clinical trial", Lancet 2001;357:251-6.

Setnikar I. "Glucosamine for osteoarthritis. Sound science might have helped avoid confusion", BMJ 2001; 323:1003-4.Lj Osteoarthritis and Cartilage, No. . . 9.

Bassleer C., et al., "Stimulation of proteoglycan production by glucosamine sulfate in chondrocytes isolated from human osteoarthritic articular cartilage in vitro", Osteoarthritis Cartilage 1998;6: 427-34.

Demattei, M., et al., "High doses of glucosamine-HCl have detrimental effects on bovine articular cartilage explants cultured in vitro", Osteoarthritis Cartilage 2002;10:816-25.

Lavert, S., et al., "Synovial fluid levels and serum pharmacokinetics in a large animal model following treatment with oral glucosamine at clinically relevant doses", Arthritis Rheum 2005;52:181-91.

Biggee, B., et al., "Low levels of human serum glucosamine after ingestion of glucosamine sulphate relative to capability for peripheral effectiveness", Ann Rheum Dis 2006;65:222-6.

Persiani, S., et al., "Glucosamine oral bioavailability and plasma pharmacokinetics after increasing doses of crystallne glucosamine sulfate in man", Osteoarthritis Cartilage 2005;13:1041-9.

Tiraloche, G., et al., "Effect of oral glucosamine on cartilage degradation in a rabbit model of osteoarthritis", Arthritis Rheum 2005;52: 1118-28.

Noyszewski, E., et al., "Preferential incorporation of glucosamineinto the galactosamine moieties of chondroitin sulfates in articular cartilage explants", Arthritis Rheum 2001;44:1 089-95.

Fenton, J., et al., "Glucosamine HCI reduces equine articular cartilage degradation in explant culture", Osteoarthritis Cartilage 2000;8:258-65.

Gouze, I., et al., "Glucosamine modulates IL-1-induced activation of rat chondrocytes at a receptor level, and by inhibiting theNF-kappa B pathway", FEBS Lett 2002;510:166-70.

Largo, R., et al., "Glucosamine inhibits IL-1beta-induced NFkappaB activation in human osteoarthritic chondrocytes", Osteoarthritis Cartilage 2003;11 :290-8.

Meininger, C., et al., "Glucosamine inhibits inducible nitric oxide synthesis", Biochem Biophys Res Commun 2000;279:234-9.

Derfoul, A., et al., "Glucosamine promotes chondrogenic phenotype in both chondrocytes and mesenchymal stem cells and inhibits Il-1 beta induced . . .", 51st Annual Meeting of the Oithopedic Research Society, 2005; Poster No: 1477.

Mroz, et al., "Use of 3H-glucosamine and 35Ssulfate with cultured humanchondrocytes to determine the effect of glucosamine concentration on formation of chondroitin sulfate", Arthritis Rheum 2004; 50:3574-9.

Kim, T., et al., "Experimental model for cartilage tissue engineering to regenerate the zonal organization of articular cartilage", OSteoarthritis Cartilage 2003;11 :653-64.

Altman S., et al., "Comparison of trypan blue dye exclusion and fluorometric assays for mammalian cell viability determinations", Biotechnol Prog 1993;9:671-4.

Kim,Y., et al., Fluorometric assay of DNA in cartilage explants using Hoechst 33258. Anal Biochem 1988;174:168-76.

Farndale, R., et al., "Improved quantification and discrimination of sulphated glycosaminoglycans by use of dimethyl methylene blue", Biochem Biophys Acta 1986;883:173-7.

Stegemann, H., et al., "Determination of hydroxyproline", Clin Chim Acta 1967;18:267-73.

Freed, L., et al., Tissue Engineering of Cartilage. The Biomedical Engineering Handbook. Boca Raton, FL: CRC Press 1995:1778-96.

Cukierman, E., et al., "Taking cell-matrix adhesions to the third dimensions", Science 2001;294:1708-12.

Jiang, H., et al., "Cell-matrix entanglement and mechanical anchorage of fibroblasts in threedimensional collagen matrices", Mol Bioi Cell 2005; 16:5070-6.

Varghese, S.,J et al., Hydrogels for musculoskeletal tissue engineering. Adv Polym Sci 2006; doi: 10.1007/12_072.

* cited by examiner

GLUCOSAMINE MATERIALS

RELATED APPLICATIONS

This application is a Continuation of U.S. application Ser. No. 11/816,600, filed Aug. 17, 2007 now abandoned and entitled "Glucosamine Materials"; which is a National Stage Application of PCT/US2006/005748, filed Feb. 17, 2006 and entitled "Glucosamine Materials"; which claims the benefit of U.S. Provisional Application No. 60/654,151, filed Feb. 18, 2005 and entitled "Glucosamine Materials". The content of these applications are herein incorporated by reference in their entireties for all purposes.

BACKGROUND OF THE INVENTION

Hyaluronic acid derivatives have been described, U.S. Pat. Nos. 6,699,471; 6,723,709; 5,502,081; 5,616,568; 5,502,081; 6,537,979; 6,294,202; 6,703,041; 6,610,669; 6,749,865; and 6,521,223. Many of those derivatives are used primarily to reduce adhesions at sites of surgical intervention.

A chemically modified hyaluronic acid and carboxymethylcellulose combination is commercially available in film form (Seprafilm™, Genzyme), U.S. Pat. Nos. 4,937,270 and 5,017,229.

Generally, the hyaluronic acid derivatives have physical and chemical properties that differ from the native compound, the derivatives have higher residence time, generally owing to increased viscosity, and can be manufactured into devices without losing many of the biocompatible properties of the native compound. Such modifications are required because hyaluronic acid is characterized by a very rapid absorption. Nevertheless, hyaluronic acid is attractive because the molecule is not covalently bound to protein.

Kulkarni (U.S. Pat. No. 6,822,064) teaches polymerized macromers containing, for example, N-acetylglucosamine (NAG). The molecules of interest comprise a backbone molecule to which NAG, among many other sugars, is covalently bound. The macromers bind to and inactivate lysozyme. The macromers are stable and resistant to degradation.

SUMMARY OF THE INVENTION

It is an object of the invention to provide compositions of various forms for use as devices and vehicles in a body. The compositions can be in liquid or solid form. Thus, an object is to provide, for example, a replacement synovial fluid; a scaffold for tissue engineering; a film for wound healing, shaping or for lining or coating a surface; a form for drug delivery; a nutrient and so on.

Those and other objects have been attained in the development of polymeric glucosamine (GlcN) derivatives such as polyGlcN, functionalized hyaluronic acid and biodegradable polymers comprising a backbone to which plural GlcN residues are bound, preferably by biologically labile bonds. Suitable biomolecules that can be conjugated with GlcN include, for example hyaluronic acid and chondroitin sulfate.

In other embodiments, the GlcN residues are functionalized as known in the art. For example, one or more of the hydroxyl groups can be acetylated, for example, using acetic anhydride, to yield acetylated GlcN residues. Other suitable functional groups that can be added to the GlcN residue include carboxyl groups. Also, the amine group of GlcN can be derivatized.

In other embodiments, the polyGlcN or biologically compatible polymers carrying plural GlcN residues contain biologically labile bonds so that the molecules are biodegradable. That makes the monomers or oligomers of the polymer and the GlcN residues, functionalized or not, biologically available.

Additional features and advantages of the present invention are described in, and will be apparent from, the following Detailed Description of the Invention and the figures.

BRIEF DESCRIPTION OF THE FIGURES

In FIG. 4A, HA is derivatized. Again, a reactive GlcN residue can be made by the schemes set forth in FIG. 1 or 2, and reacted with the derivatized HA to conjugate the two molecules, FIG. 4B.

DETAILED DESCRIPTION OF THE INVENTION

Figure 1:
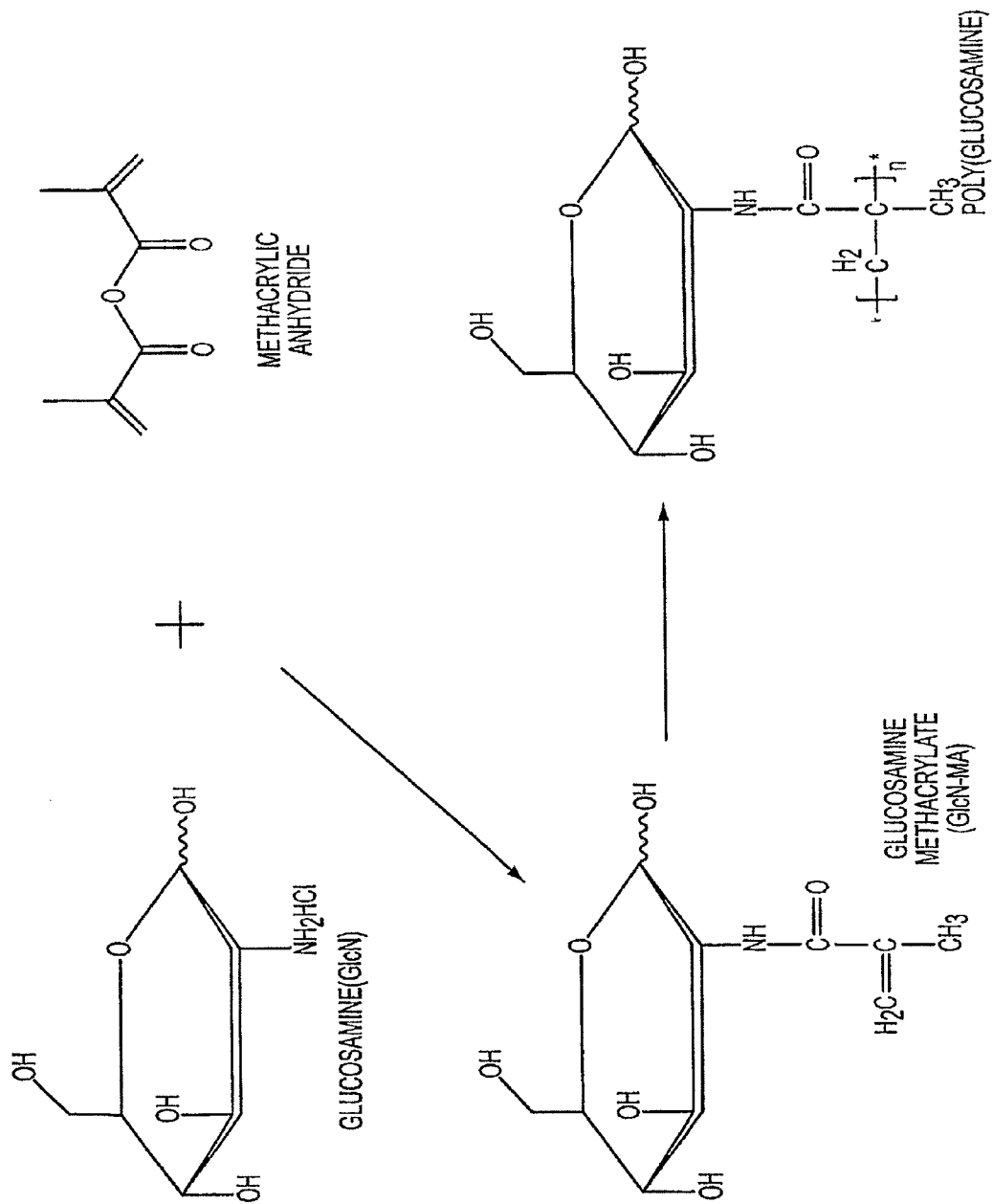
FIG. 1 depicts a synthetic scheme for making a polyGlcN molecule.

The invention relates to products and methods for making and using GlcN molecules for a variety of uses, including structural, supportive, nutritive, lubricative and so on.

The glucosamine molecules of interest can assume a variety of forms depending on the degree of polymerization, degree of bonding, the substituents attached to a glucosamine and the molecules to which a glucosamine are attached.

In one embodiment, a molecule of interest is a polyGlcN molecule. GlcN residues are linked to form a polymer using standard chemistries. Thus, GlcN can be functionalized to produce monomers suitable for polymerization. On exposure to a polymerizing initiator, polyGlcN is formed.

A "polymerizing initiator" refers to any substance that can initiate polymerization of monomers or polymers by, for example, free radical generation, The polymerizing initiator often is an oxidizing agent. Exemplary polymerizing initiators include those which are activated by exposure to, for example, electromagnetic radiation, such as UV light or heat.

In another embodiment, a molecule of interest comprises a biological molecule or biocompatible molecule, a backbone molecule, to which one or more GlcN residues are attached, preferably by biologically labile linkages. Generally, the backbone molecule is a polymer. Accordingly, each monomer can be derivatized with a GlcN residue, every other monomer can contain a GlcN, and so on, as a design choice. A molecule of interest contains plural GlcN residues. The backbone molecule can be any biological molecule such as a carbohydrate, a polynucleotide or a polypeptide. The GlcN is bound to the backbone molecule, preferably by a chemical bond that is biodegradable in situ. Suitable polymers include those that are naturally occurring in synovial fluid, cartilaginous environments and osseous environments. Suitable biomolecules that can serve as a backbone include polysaccharides. Suitable polysaccharides include hyaluronic acid and chondroitin sulfate, for example.

Alternatively, the backbone can be a heteropolymer of glucosamine and another monomer, such as a hyaluronic acid component or a chondroitin sulfate component. Such naturally occurring polymers that are preferred are those which are biodegradable. The GlcN residue is bound thereto using standard chemistries.

The term "polymer" is used to refer to molecules composed of repeating monomer units, including homopolymers, block copolymers, heteropolymers, random copolymers, graft copolymers and so on. Polymers also include linear polymers as well as branched polymers. The branched polymers of interest are not highly branched, are not generational polymers, known as dendrimers or starburst polymers.

A "monomer" is the basic repeating unit in a polymer. A monomer may itself be a monomer or may be dimer or oligomer of at least two different monomers, and each dimer or oligomer is repeated in a polymer.

The term "biologically compatible polymer" or "biocompatible" refers to a naturally occurring polymer or one that is not toxic to the host. Generally, the metabolites of the polymer of interest also are not toxic to the host. It is not necessary that any subject composition have a purity of 100% to be deemed biocompatible; indeed, it is only necessary that the subject compositions be non-toxic to the host. Hence, a subject composition may comprise monomer, polymers or portions thereof comprising 99%, 98%, 97%, 96%, 95%, 90%, 85%, 80%, 75% or even less of biocompatible monomer, polymers or portions thereof, e.g., including monomers, polymers or portions thereof, and other materials and excipients described herein, and still be biocompatible.

To determine whether a polymer or other material is biocompatible, it may be necessary to conduct a toxicity analysis. Such assays are well known in the art. One example of such an assay may be performed with, for example, live carcinoma cells in the following manner: a sample of the intact molecule or a sample wherein the molecule is degraded in 1M NaOH at 37° C. until complete degradation is observed is used. The solution is then neutralized with 1M HCl. About 200 pL of various concentrations of the sample are placed in 96-well tissue culture plates and seeded with human carcinoma cells at $10^4$/well density. The samples are incubated with the cells for 48 hours. The results of the assay may be plotted as % relative growth vs. concentration of sample in the tissue culture well. In addition, monomers, polymers, polymer structures and formulations of the present invention may also be evaluated by well-known in vivo tests, such as subcutaneous implantation in rats to confirm that they do not cause significant levels of irritation or inflammation at the subcutaneous implantation sites. Acceptable levels of toxicity are as known in the art.

A GlcN molecule of interest is one that is not toxic to a host, such as a mammal. Determining safety in a host is a well known exercise in the food and drug arts, and includes, for example, in vitro studies on cells and tissues, and perhaps, organs, animal studies and early human clinical trials.

In some embodiments, the disclosure is directed to a composition comprising a glycosaminoglycan, mucopolysaccharide, collagen or proteoglycan component, such as hyaluronic acid, heparin sulfate, glucosamines, dermatans, keratans, heparans, hyalurunan, aggrecan and the like, or a saccharide, such as hyaluronic acid, heparin sulfate, keratan sulfate and the like serving as the backbone molecule. Those polysaccharides are natural components of extracellular matrices of cells and tissues. However, in general, any biologically compatible polymer can be used as the polymer backbone.

Synthetic polymers that are biocompatible also can be used in the practice of the instant invention. Examples of such synthetic, biocompatible polymers are polyethylene glycol (PEG), polyvinyl alcohol (PVA) and block copolymers, such as the Pluronic® compounds.

Suitable polymers include biocompatible monomers with recurring units found in poly(phosphoesters), poly(lactides), poly(glycolides), poly(caprolactones), poly(anhydrides), poly(amides), poly(urethanes), poly(esteramides), poly (orthoesters), poly(dioxanones), poly(acetals), poly(ketals), poly(carbonates), poly(orthocarbonates), poly(phosphazenes), poly(hydroxybutyrates), poly(hydroxyl valerates), poly(alkylene oxalates), poly(alkylene succinates), poly (malic acids), poly(amino acids), poly(vinylpyrrolidone), poly(ethylene glycol), poly(hydroxycellulose), chitin and chitosan, and copolymers, terpolymers or combinations or mixtures of the above materials.

Other suitable synthetic polymers include polymers containing amine groups, such as chemically synthesized polypeptides. Such polypeptides may include polynucleophilic polypeptides that have been synthesized to incorporate amino acids containing primary amino groups for example, lysine and/or amino acids containing thiol groups (such as cysteine). Further suitable synthetic polymers include poly (amino)acids.

A GlcN derivative of interest can be configured to have varying levels of biodegradability by the type and number of bonds between monomers. Thus, very labile bonds can be used for a composition destined for rapid degradation and more resistant bonds can be used for compositions meant for a desired level of permanence in a host. By being biodegradable, the GlcN residues, functionalized or not, become biologically available.

By biodegradable is meant that the polymer or particular bonds of the polymer are cleaved under normal physiological processes in a mammal. Generally, the polymer degradation products are non-toxic or biocompatible as well.

The term "biodegradable" is art-recognized and is intended to indicate that an object degrades during use. In general, degradation attributable to biodegradability involves the degradation of a biodegradable polymer into oligomers or its component subunits, or digestion, e.g., by a biochemical process, of the polymer into smaller subunits. In certain embodiments, two different types of biodegradation may generally be identified. For example, one type of biodegradation may involve cleavage of bonds (whether covalent or otherwise) in the polymer backbone. In such biodegradation, monomers and oligomers typically result, and even more typically, such biodegradation occurs by cleavage of a bond connecting one or more of subunits of a polymer. In contrast, another type of biodegradation may involve cleavage of a bond (whether covalent or otherwise) internal to a side chain or that connects a side chain to the polymer backbone. The side chain is one that contains GlcN. Alternatively, a therapeutic agent, biologically active agent or other chemical moiety attached as a side chain to a polyGlcN may be released by biodegradation. In certain embodiments, one or the other or both general types of biodegradation may occur during use of a polymer of interest. As used herein, the term "biodegradation" encompasses both general types of biodegradation as the overall desired function of the functionalized polymer of interest wanes.

The degradation rate of a biodegradable polymer often depends in part on a variety of factors, including the chemical identity of linkages; the molecular weight, crystallinity, biostability and degree of cross-linking of such polymer; the physical characteristics of the implant, such as the shape and size; the mode and location of administration; and so on. For example, the greater the molecular weight, the higher the degree of crystallinity, and/or the greater the biostability, the biodegradation of any biodegradable polymer is usually slower. The term "biodegradable" is intended to cover materials and processes also termed "bioerodible". Generally, the rate of degradation is a design choice based on the monomers, functional groups, added ingredients and the like that are used.

In certain embodiments, the biodegradation rate of such polymer may be characterized by the presence of enzymes, for example, a particular protease, lipase, saccharidase and so on. In such circumstances, the biodegradation rate may depend on not only the chemical identity and physical characteristics of the polymer matrix, but also on the identity, use, presence and the like of any such enzyme.

Thus, a GlcN molecule of interest can be one that releases GlcN residues thereby making the GlcN molecule bioavailable, but also one that releases monomers or oligomers of the backbone molecule. GlcN is a naturally occurring molecule and has nutritive and effector functions. GlcN, for example, is compatible and promotes stem cell growth and differentiation, for example, of mesenchymal stem cells to form chondrocytes. GlcN can have a role in tissue development and repair, such as cartilage growth and development, in general. Therefore, placing a GlcN composition of interest into a bone or cartilage defect, whether arising by normal wear and tear, from an injury or purposely to stimulate repair, such as by microfracture, can serve not only a structural role by filling the defect and providing structural support, but also a nutritive role by stimulating stem cell differentiation, and by stimulating bone and cartilage growth. A composition that provides a 1 mM to about a 10 mM local concentration of GlcN is beneficial. Other concentrations, such as 2-5 mM can be advantageous. An artisan can determine a suitable local concentration of GlcN practicing methods known in the pharmaceutic arts, and that determination will govern the nature and composition of the GlcN composition of interest to obtain the desired concentration of GlcN.

GlcN monomers and biodegradable polymers of GlcN, which contain GlcN or which release GlcN, may be incorporated into other matrices, such as hydrogels, fibers, scaffolds, depots, prostheses, nanofibers and other structures, for release from the matrix in a fashion and at a rate determinable as a design choice depending on, for example, matrix pore size, ionic interactions between GlcN and the matrix, degree of polymerization of a GlcN polymer, degree of derivatization of a GlcN or matrix and so on. Generally, the biomaterial, such as a scaffold, is one that is biodegradable. Nanomaterials, such as nanotubes and nanofibers, can be incorporated into such scaffolds and other matrices, or may comprise the matrix per se. See for example, WO 2005/123903.

A GlcN molecule of interest, whether a monomer of part of a polymer, may be functionalized to contain reactive groups. That enables a GlcN molecule of interest to be covalently attached to a matrix, tissue and the like, or enables a GlcN molecule of interest to contribute to a biomaterial. Thus a functionalized GlcN molecule of interest can react with a functionalized-polymer or functionalized hydrogel.

A reactive moiety includes any moiety that reacts with a suitable element, chemical group or chemical site on a target entity. One set of target entities are biological structures, such as cells, tissues, organs and the like. A functional group on the biologically compatible polymer reactive with a biological surface moiety includes any functional group that reacts with a suitable element, chemical group or chemical site on a surface of a biological structure, such as a cell, tissue, organ and the like. Thus, a suitable element, chemical group or chemical site on the surface of a biological structure would be a reactive group found in, for example, a carbohydrate, an amino acid or a nucleic acid, such as an amine group, a carboxylic acid group, a hydroxyl group, a sulfate group and so on. Accordingly, a suitable reactive moiety would be one that reacts with an amine group, a hydroxyl group and so on of the surface of a biological structure. A suitable functional group would be one that reacts with an amine group, a hydroxyl group and so on of the surface of a biological structure. Another example is an aldehyde group.

Other reactive moieties are those which react with elements, chemical groups or chemical sites on biologically compatible materials, such as implants, prostheses, other devices and the like.

Other functional groups on the biologically compatible polymer are those which react with elements, chemical groups or chemical sites on a bridging molecule.

A reactive moiety or functional group (which terms, for the purposes of the invention, are considered equivalent) may include alkenyl moieties such as acrylates, methacrylates, dimethacrylates, oligoacrylates, oligomethacrylates, ethacrylates, itaconates or acrylamides. Further reactive moieties include carboxylates and aldehydes. Other reactive moieties may include ethylenically unsaturated monomers including, for example, alkyl esters of acrylic or methacrylic acid such as methyl methacrylate, ethyl methacrylate, butyl methacrylate, ethyl acrylate, butyl acrylate, hexyl acrylate, n-octyl acrylate, lauryl methacrylate, 2-ethylhexyl methacrylate, nonyl acrylate, benzyl methacrylate, the hydroxyalkyl esters of the same acids such as 2-hydroxyethyl acrylate, 2-hydroxyethyl methacrylate, and 2-hydroxypropyl methacrylate, the nitrile and amides of the same acids such as acrylonitrile, methacrylonitrile, methacryl amide, vinyl acetate, vinyl propionate, vinylidene chloride, vinyl chloride, and vinyl aromatic compounds such as styrene, t-butyl styrene and vinyl toluene, dialkyl maleates, dialkyl itaconates, dialkyl methylene malonates, isoprene and butadiene. Suitable ethylenically unsaturated monomers containing carboxylic acid groups include acrylic monomers such as acrylic acid, methacrylic acid, ethacrylic acid, itaconic acid, maleic acid, fumaric acid, monoalkyl itaconate including monomethyl itaconate, monoethyl itaconate, and monobutyl itaconate, monoalkyl maleate including monomethyl maleate, monoethyl maleate, and monobutyl maleate, citraconic acid and styrene carboxylic acid. Suitable polyethylenically unsaturated monomers include butadiene, isoprene, allylmethacrylate, diacrylates of alkyl diols such as butanediol diacrylate and hexanediol diacrylate, divinyl benzene and the like.

In some embodiments, a monomer of a biologically compatible polymer may be functionalized through one or more thio, carboxylic acid or alcohol moiety located on a monomer of the biopolymer.

The reactive moieties or functional groups are attached to the monomer or biologically compatible polymer using known chemistries based on design choice.

Thus, in producing, for example, a functionalized saccharide, a solution comprising the saccharide and a first functional group reactant, such as an alkylene or an acrylate group, are mixed. The solution is stirred, for example, for at least 10 days, at least 11 days or at least 15 days. Alternatively, the solution may be stirred or maintained for about 10 to about 15 days or about 14 to about 15 days. The solution may include a polar solvent, for example an aqueous solvent.

For example, methacrylic anhydride, methacryloyl chloride and glycidyl methacrylate may be used to add methacrylate groups to one or more monomers of a polymer chain. Glycidyl methacrylate may be used, for example, for efficiency of reaction. Further, the modification reagents may be chosen to optimize for a lack of cytotoxic byproducts.

A suitable method for making a polymer with aldehyde groups is to treat a molecule with adjacent hydroxyl groups, such as chondroitin sulfate, with a periodate salt, as known in the art.

The term "functionalized" refers to a modification of an existing molecular entity, structure or site to generate or to introduce a new reactive or more reactive group, such as an acetyl group or a group (e.g., acrylate group) that is capable of undergoing reaction with another functional group (e.g., a sulfhydryl group) to form, for example, a covalent bond. For example, carboxylic acid groups can be functionalized by reaction with an acyl halide, e.g., an acyl chloride, again, using known procedures, to provide a new reactive functional group in the form of an anhydride.

The term "aliphatic" is an art-recognized term and includes linear, branched and cyclic alkanes, alkenes or alkynes. In certain embodiments, aliphatic groups in the present invention are linear or branched and have from 1 to about 20 carbon atoms, or more.

The term "alkyl" is art-recognized and includes saturated aliphatic groups, including straight-chain alkyl groups, branched-chain alkyl groups, cycloalkyl (alicyclic) groups, alkyl substituted cycloalkyl groups and cycloalkyl substituted alkyl groups. In certain embodiments, a straight chain or branched chain alkyl has about 30 or fewer carbon atoms in its backbone (e.g., $C_1$-$C_{30}$ for straight chain and $C_3$-$C_{30}$ for branched chain), and alternatively, about 20 or fewer carbon atoms. Likewise, cycloalkyls have from about 3 to about 10 carbon atoms in their ring structure, and alternatively, about 5, 6 or 7 carbons in the ring structure.

Moreover, the term "alkyl" (or "lower alkyl") includes both "unsubstituted alkyls" and "substituted alkyls", the latter of which refers to alkyl moieties having substituents replacing a hydrogen on one or more carbons of the hydrocarbon backbone. Such substituents may include, for example, a halogen, a hydroxyl, a carbonyl (such as a carboxyl, an alkoxycarbonyl, a formyl or an acyl), a thiocarbonyl (such as a thioester, a thioacetate or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate) and silyl groups, as well as ethers, alkylthios, carbonyls (including ketones, aldehydes, carboxylates and esters), —$CF_3$, —CN and the like. Exemplary substituted alkyls are described below. Cycloalkyls may be further substituted with alkyls, alkenyls, alkoxys, alkylthios, aminoalkyls, carbonyl-substituted alkyls, —$CF_3$, —CN and the like.

The term "aralkyl" is art-recognized and includes aryl groups (e.g., an aromatic or heteroaromatic group).

The terms "alkenyl" and "alkynyl" are art-recognized and include unsaturated aliphatic groups analogous in length and possible substitution of the alkyls described above, but that contain at least one double or triple bond, respectively.

Unless the number of carbons is otherwise specified, "lower alkyl" refers to an alkyl group, as defined above, but having from one to ten carbons, alternatively, from one to about six carbon atoms in the backbone structure. Likewise, "lower alkenyl" and "lower alkynyl" have similar chain lengths.

A "methacrylate" refers to a vinylic carboxylate, for example, a methacrylic acid in which the acidic hydrogen has been replaced. Representative methacrylic acids include acrylic, methacrylic, chloroacrylic, cyano acrylic, ethylacrylic, maleic, fumaric, itaconic and half esters of the latter dicarboxylic acids.

The term "heteroatom" is art-recognized and in an organic molecule, generally includes an atom of any element other than carbon or hydrogen. Illustrative heteroatoms include boron, nitrogen, oxygen, phosphorus, sulfur and selenium.

The term "aryl" is art-recognized and includes, for example, 5-, 6- and 7-membered single ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls, or rings joined by non-cyclic moieties.

The terms "ortho", "meta" and "para" are art-recognized and apply to 1,2-, 1,3- and 1,4-disubstituted benzenes, respectively. For example, the names 1,2-dimethylbenzene and ortho-dimethylbenzene are synonymous.

The terms "heterocyclyl" and "heterocyclic group" are art-recognized and include 3- to about 10-membered ring structures, such as 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams, such as azetidinones and pyrrolidinones, sultams, sultones and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, allylthio, sulfonyl, ketone, aldehyde, ester, a heterocyclyl, an aromatic or heteroaromatic moiety, —$CF_3$, —CN or the like.

The terms "polycyclyl" and "polycyclic group" are art-recognized and include structures with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms, e.g., three or more atoms are common to both rings, are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN or the like.

The following art-recognized terms have the following meanings: "nitro" means —$NO_2$; the term "halogen" designates —F, —Cl, —Br or —I; the term "sulfhydryl" means —SH; the term "hydroxyl" or "hydroxy" means —OH; and the term "sulfonyl" means —$SO_2$—.

The terms "amine" and "amino" are art-recognized and include both unsubstituted and substituted amines, as well as primary, secondary tertiary amines, which may be functionalized. The term "alkylamine" includes an amine group, as defined above, having a substituted or unsubstituted alkyl attached thereto. The term "acylamino" is art-recognized and includes a amine having a substituted or unsubstituted acyl group attached thereto. The term "amido" is art-recognized as an amino-substituted carbonyl. In certain embodiments, the amide will not include imides which may be unstable.

Certain monomeric subunits of the present invention may exist in particular geometric or stereoisomeric forms. In addition, polymers and other compositions of the present invention may also be optically active. The present invention contemplates all such compounds, including cis and trans isomers, R and S enantiomers, diastereomers, d isomers, l isomers, the racemic mixtures thereof, and other mixtures thereof, as falling within the scope of the invention. Additional asymmetric carbon atoms may be present in a substituent, such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino or an acidic functional group, such as carboxyl, diastereomeric salts are formed with an appropriate optically active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with the permitted valency of the substituted atom and the substituent, and that the substitution results in a stable compound, e.g., which does not spontaneously undergo transformation, such as by rearrangement, cyclization, elimination or other reaction.

The term "substituted" is also contemplated to include all permissible substituents of organic compounds. In a broad aspect, the permissible substituents include acyclic and cyclic, branched and unbranched, carbocyclic and heterocyclic, and aromatic and non-aromatic substituents of organic compounds. Illustrative substituents include, for example, those described hereinabove. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986-87, inside cover.

In some embodiments, the number of the reactive moieties per polymeric unit may be at least one moiety per about 10 monomeric units, or at least about 2 moieties per about 10 monomeric units. Alternatively, the number of reactive moieties per polymeric unit may be at least one moiety per about 12 monomeric units, or per about 14 monomeric units. For example, there may be at least about one reactive moiety per 15 or more monomeric units. The number of moieties also can range from one per monomer, one per two monomers, one per three monomers, one per 4, 5, 6, 7, 8 or 9 monomers.

Also, a polymer of interest may contain plural species of reactive moieties to provide a directionality to the polymer. When, for example, a polymer contains two species of reactive moieties, the ratio of one of the two reactive moieties to the other can be 5:1, 9:2, 4:1, 7:2, 3:1, 5:2, 2:1, 3:2, 1:1, 2:3, 1:2, 2:5, 1:3, 2:7, 1:4, 2:9 or 1:5 along the full length of the polymer. Preferably, each of the functional moieties is regularly distributed along the length of the polymer and in substantially equal molar amounts. However, the amount of any one reactive moiety type is optimized for reaction with the intended target entity and may result in amounts where the ratio of the two types of reactive moieties deviates from unity.

For example, poly(ethylene oxide)-diacrylate (PEODA) may be used, and cross-linked polymer matrices may include cogels of an acrylated GlcN and PEODA. The cogels formed thereby will have properties different from that of the two parent compounds, and properties of the cogel will vary based on the ratio of the two reactants. Examples of derivatized hydrogels can be found in WO 2004/029137.

The mechanical properties of a polymer or a multi-layer polymer, such as a scaffold, may also be related to the pore structure. For applications in tissue engineering, scaffolds with different mechanical properties are produced depending on the desired clinical application. For example, scaffolds for cartilage tissue engineering in the articular joint must survive higher mechanical stresses than a cartilage tissue engineering system in other body sites. Thus, hydrogels with mechanical properties that are easily manipulated may be desired.

Cytotoxicity of the biopolymer scaffold system may be evaluated with any suitable cells, such as fibroblasts, by, for example, using a live-dead fluorescent cell assay and a suitable indicator of viability, such as a vital stain, such as a tetrazolium dye, such as MTT, a compound that actively metabolizing cells convert from yellow to purple.

Certain GlcN molecules of interest can serve as carriers of pharmaceutically active agents, biologically active agents and the like. The carrying function can be non-specific wherein the active agent non-specifically becomes associated with a GlcN molecule of interest. Biologically active agents may be incorporated into the polymer by mere admixture. That can result in encapsulation, entrapment or engulfment by a GlcN-containing structure, such as cochleates, vesicles, pouches and the like.

Alternatively, the agents may be incorporated into a multi-layer polymer or attached to a polymer of interest by binding these agents to the functional groups on the polymers. Such compositions may include linkages that can be easily biodegraded, for example as a result of enzymatic degradation, resulting in the release of the active agent into the target tissue, where it will exert its desired therapeutic effect.

A simple method for incorporating biologically active agents containing nucleophilic groups into the polymer involves mixing the active agent with a polyelectrophilic component prior to addition of the polynucleophilic component. By varying the relative molar amounts of the different components of the reactive composition, it is possible to alter the net charge of the resulting polymer composition, for example, to prepare a composition for the delivery of a charged compound, such as a protein or ionizable drug. As such, the delivery of charged proteins or drugs, which would normally diffuse rapidly out of a neutral carrier, can be controlled.

For example, if a molar excess of a component that is polynucleophilic is used, the resulting composition may have a net positive charge and can be used to ionically bind and deliver negatively charged compounds. Examples of negatively charged compounds that can be delivered from these matrices include various drugs, cells, proteins and polysaccharides.

If a molar excess of a component that is polyelectrophilic is used, the resulting composition has a net negative charge and can be used to ionically bind and deliver positively charged compounds. Examples of positively charged compounds that can be delivered from these matrices include various drugs, cells, proteins, and polysaccharides.

The terms "active agent," "pharmaceutically active agent" and "biologically active agent" are used interchangeably herein to refer to a chemical or biological compound that induces a desired physical, pharmacological or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc. As described herein, a biologically active agent includes a living entity, such as a virus, microbe or cell.

The biologically active agent may vary widely with the intended purpose for the composition. The term "active" is art-recognized and refers to any chemical moiety that has a biological, physiological or pharmacological activity that acts locally or systemically in a subject. Examples of biologically active agents, that may be referred to as "drugs", are described in well-known literature references such as the Merck Index, the Physicians Desk Reference and The Pharmacological Basis of Therapeutics, and include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a biologically active agent may be used which are capable of being released by the subject composition, for example, into adjacent tissues or fluids on administration to a subject.

Further examples of biologically active agents include, without limitation, enzymes, receptor antagonists or agonists, hormones, growth factors, autogenous bone marrow, antibiotics, antimicrobial agents and antibodies. The term "biologically active agent" is also intended to encompass various cell types and nucleic acids that can be incorporated into the compositions of the invention. Thus, a GlcN composition can contain collagen and other biological molecules. The GlcN composition can contain other molecules associated with cell tissue and biological adhesion in general, such as RGD peptides.

In certain embodiments, the subject compositions comprise about 1% to about 75% or more by weight of the total composition, alternatively about 2.5%, 5%, 10%, 20%, 30%, 40%, 50%, 60%, 70% or more, of a biologically active agent.

Non-limiting examples of biologically active agents include following: adrenergic blocking agents, anabolic agents, androgenic steroids, antacids, anti-asthmatic agents, anti-allergenic materials, anti-cholesterolemic and anti-lipid agents, anti-cholinergics and sympathomimetics, anti-coagulants, anti-convulsants, anti-diarrheal, anti-emetics, anti-hypertensive agents, anti-infective agents, anti-inflammatory agents such as steroids, non-steroidal anti-inflammatory agents, anti-malarials, anti-manic agents, anti-nauseants, anti-neoplastic agents, anti-obesity agents, anti-parkinsonian agents, anti-pyretic and analgesic agents, anti-spasmodic agents, anti-thrombotic agents, anti-uricemic agents, antianginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, agents, hyperglycemic agents, hypnotics, hypoglycemic agents, ion exchange resins, laxatives, mineral supplements, mitotics, mucolytic agents, growth factors, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, antigenic materials and pro-drugs.

Specific examples of useful biologically active agents the above categories include: (a) anti-neoplastics such as androgen inhibitors, antimetabolites, cytotoxic agents and immunomodulators; (b) anti-tussives such as dextromethorphan, hydrobromide, noscapine, carbetapentane citrate and chlophediol hydrochloride; (c) antihistamines such as chlorpheniramine phenindamine tartrate, pyrilamine doxylamine succinate and phenyltoloxamine citrate; (d) decongestants such as hydrochloride, phenylpropanolamine hydrochloride, pseudoephedrine hydrochloride and ephedrine; (e) various alkaloids such as codeine phosphate, codeine sulfate and morphine; (f) mineral supplements such as potassium chloride, zinc chloride, calcium carbonate, magnesium oxide and other alkali metal and alkaline earth metal salts; (g) ion exchange resins; (h) antipyretics and analgesics such as acetaminophen, aspirin and ibuprofen; (i) appetite suppressants such as phenyl-propanolamine or caffeine; (j) expectorants such as guaifenesin; (k) antacids such as aluminum hydroxide and magnesium hydroxide; (l) biologicals such as peptides, polypeptides, proteins and amino acids, hormones, interferons, cytokines and other bioactive peptidic compounds, such as calcitonin, ANF, EPO and insulin; (m) antiinfective agents such as anti-fungals, anti-virals, antiseptics and antibiotics; and (n) desensitizing agents and antigenic materials, such as those useful for vaccine applications.

Biologically active agents also include living entities, such as cells. Thus, for example, mesenchymal stem cells can be attached to or entrapped within a matrix comprising the polymers of interest. Mesenchymal stem cells may not be differentiated and therefore may differentiate to form various types of new cells due to the presence of an active agent, such as GlcN, or the effects (chemical, physical etc.) of the local tissue environment. Examples of mesenchymal stem cells include bone marrow cells, osteoblasts, chondrocytes and fibroblasts. For example, osteoblasts can be delivered to the site of a bone defect to produce new bone; chondrocytes can be delivered to the site of a cartilage defect to produce new cartilage; fibroblasts can be delivered to produce collagen wherever new connective tissue is needed; neuroectodermal cells can be delivered to form new nerve tissue; epithelial cells can be delivered to form new epithelial tissues, such as liver, pancreas etc.

The cells may be either allogeneic or xenogeneic in origin. For example, the compositions can be used to deliver cells of other species that have been genetically modified. In some embodiments, the compositions of the invention may not easily be degraded in vivo, cells entrapped within the polymer compositions will be isolated from the patient cells and, as such, should not provoke an immune response when returned to the patient.

To entrap the cells within a polymer, the cells may, for example be mixed with a composition comprising functionalized polymer, and optionally, a further biocompatible polymer. That may occur through a particular reaction or may occur during the making of a multiple layer polymer. Alternatively, the cells may be contained within a target entity attached to a polymer of interest.

Various forms of the biologically active agents may be used. These include, without limitation, such forms as uncharged molecules, molecular complexes, salts, ethers, esters, amides, and the like, which are biologically activated when implanted, injected or otherwise placed into a subject.

The polymer of the invention can also comprise additional biocompatible monomers or polymers so long as there is no interference with the desirable characteristics of the invention. Such additional monomers and polymers may offer even greater flexibility in designing the precise profile desired for, for example, targeted drug delivery, tissue engineering, enhanced administration or the precise rate of biodegradability or biocompatibility desired. Various forms advantageously can be produced including gels, foams, films and other three-dimensional structures. For example, plasticizers and stabilizing agents known in the art may be incorporated in compositions of the present invention.

A composition of this invention may further contain one or more adjuvant substances, such as fillers, thickening agents or the like. In other embodiments, materials that serve as adjuvants may be associated with the composition. Such additional materials may affect the characteristics of the composition that results. For example, fillers, such as bovine serum albumin (BSA) or human serum albumin (HSA), may be associated with the polymer composition. In certain embodiments, the amount of filler may range from about 0.1 to about 50% or more by weight of the composition, or about percent. Incorporation of such fillers may affect the sustained release rate of any encapsulated substance. Other fillers known to those of skill in the art, such as carbohydrates, sugars, starches, saccharides, celluloses and polysaccharides, including and sucrose, may be used in certain embodiments in the present invention.

Buffers, acids and bases may be incorporated in the compositions to adjust for pH. Agents to increase the diffusion distance of agents released from the composition may also be included.

The charge, lipophilicity or hydrophilicity of any subject composition may be modified by employing an additive. For example, surfactants may be used to enhance miscibility of poorly miscible liquids. Examples of suitable surfactants include sodium lauryl sulfate, betaines and other amphoteric compounds. In general, surfactants are used in low concentrations, generally less than about 5%.

The polymer, alternatively, may be formed as a solid object implantable in the anatomic area, or as a film or mesh that may be used to cover a segment of the area. Known inert ingredients can be mixed with a polymer of interest to make a suitable form such as film, scaffold, gel and so on, as taught herein. A variety of techniques for implanting solid objects in relevant anatomic areas will be likewise familiar to practitioners of ordinary skill in the art.

In some embodiments, compositions disclosed herein may be positioned in a surgically created defect that is to be reconstructed, and is to be left in this position after the reconstruction has been carried out. The present invention may be suitable for use with local tissue reconstructions, pedicle flap reconstructions or free flap reconstructions.

The reactive components of the polymer, such as monomers or oligomers, can be infused or instilled at a desired site. The present invention may be prepared to include an appropriate vehicle for this injection, implantation, infusion or direction. Once at the site, a composition of interest can be polymerized as taught herein or as known in the art. The polymer then will react with the surface of interest, such as a tissue. Thus, the polymer is "biologically anchored" to the host tissue. A suitable polymerizing initiator can be used, as known in the art.

All of the reagents necessary to make a composition of interest are commercially available or can be attained from natural sources practicing known methods.

In some embodiments, the invention is directed to kits. In certain embodiments, this invention contemplates a kit including subject compositions and instructions for use. For example, the kit may comprise a GlcN biologically compatible polymer. The kit may contain suitable instructions.

A composition of interest can comprise a polymer of interest or combinations of polymers of interest in a single solution. Thus, a synthetic synovial fluid can contain, for example, a polyGlcN and a GlcN-derivatized chondroitin sulfate. The specific amounts of each polymer can be adjusted at the design of the artisan and again the final amounts of each of the two polymers are configured such that the final solution approximates the viscosity of naturally occurring synovial fluid.

Once synthesized, the polymers are purified in a matter compatible with pharmaceutical administration, practicing methods known in the art. The biological polymers of interest are then finished in a form suitable for storage and eventual use. Thus, the biological polymers can be suspended in a biologically compatible and pharmaceutically acceptable liquid diluent or can be desiccated or freeze-dried to form a dry powder for later reconstitution and administration.

The liquid form is suitable for administration using known means, such as with a syringe and needle. Suitable amounts of replacement/supplemental fluid of interest are introduced into the body site as needed.

Suitable diluents include sterile water and biocompatible buffers such as phosphate buffered saline.

To prolong shelf life and to comply with regulatory guidelines for use with animals and humans, the reagents and components for practicing the invention, and for inclusion in a kit, can be sterilized. Chemical reagents can be exposed to forms of sterilization suitable to the reagent as known in the art. Thus, some chemical reagents can be heat sterilized, for example, using steam, or pasteurized. Other reagents can be sterilized by passage through filtration media that can remove pathogens, such as a membrane filter of appropriate pore size. Alternatively, cold sterilization techniques can be practiced to avoid using heat. Suitable cold sterilization techniques include use of ethylene oxide, irradiation, using gamma rays, x-rays, electron beams, plasma or microwaves, ozone and the like. Some of the cold sterilization techniques may be performed below ambient temperature including below 0 degrees C. The sterilization can be performed at ambient, lower or higher pressures. Also, ambient or inert atmosphere can be used. Additionally, excipients, such as sugars, organic acids, such as ascorbate or citric acid, and other stabilizers can be added to the reagents prior to sterilization.

A synthetic scheme for making a polyGlcN is set forth in FIG. 1. GlcN at a suitable concentration in a suitable buffer is mixed with methacrylate anhydride. The result of that reaction is a derivatized GlcN carrying an acrylic group. That molecule can be polymerized via the acrylate moiety.

Figure 2:
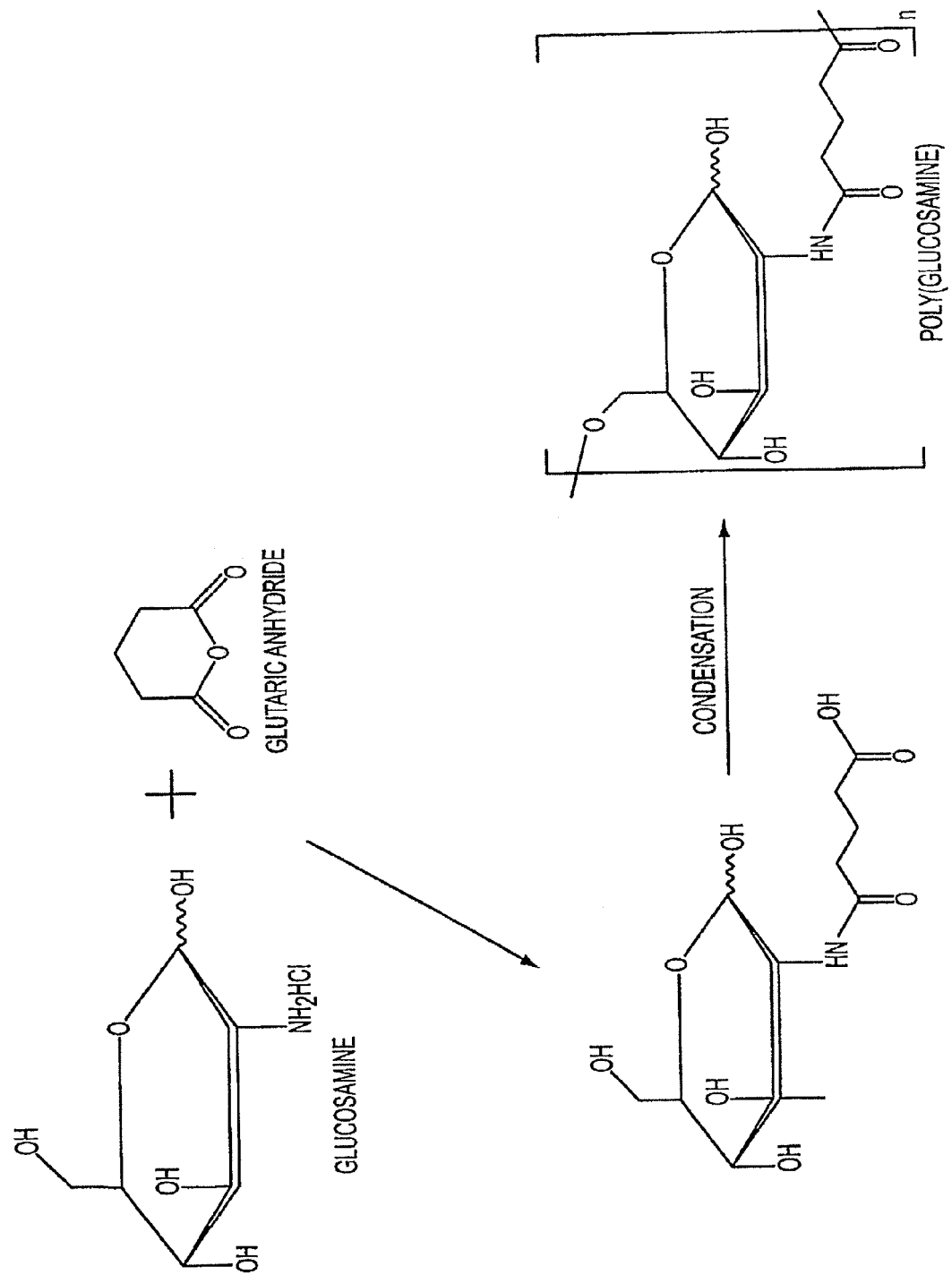
FIG. 2 depicts an alternative scheme for making a polyGlcN molecule. A GlcN is reacted with a glutamic anhydride compound.

Another form of polyGlcN is depicted in FIG. 2. Reagent grade GlcN is mixed with glutamic anhydride. The amine group of GlcN is derivatized by the anhydride group. That molecule is reacted in a condensation reaction.

Figure 3A:
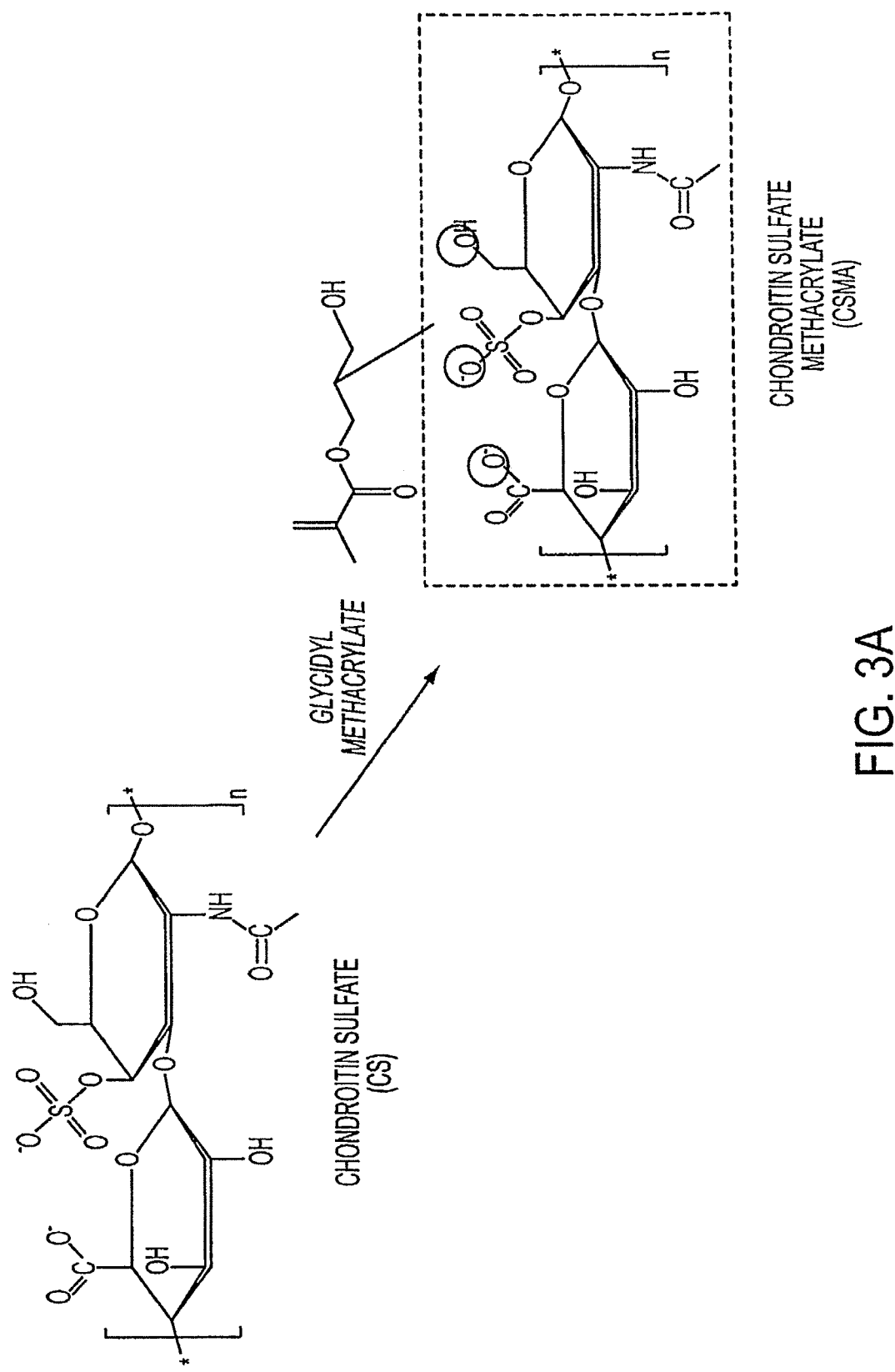
FIGS. 3A and 3B depict a synthetic scheme for conjugating GlcN onto chondroitin sulfate (CS). CS is derivatized to yield a reactive site. One such means using the known reagent, glycidyl methacrylate, and method is depicted in FIG. 3A. A reactive GlcN derivative, for example, as made by either of the schemes depicted in FIG. 1 or 2, can be reacted with the CSMA residue, FIG. 3B.
Figure 3B:
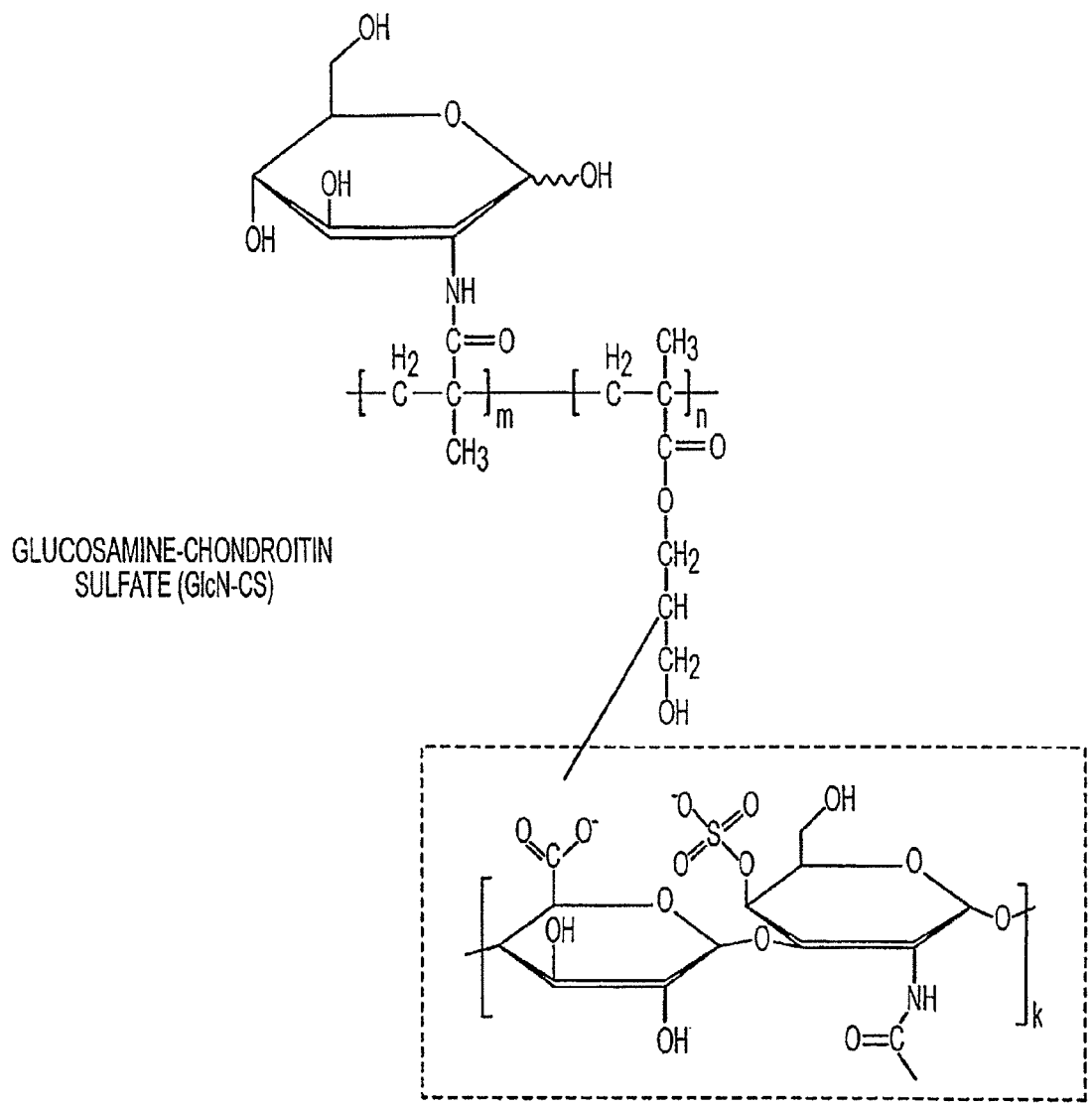
Figure 4A:
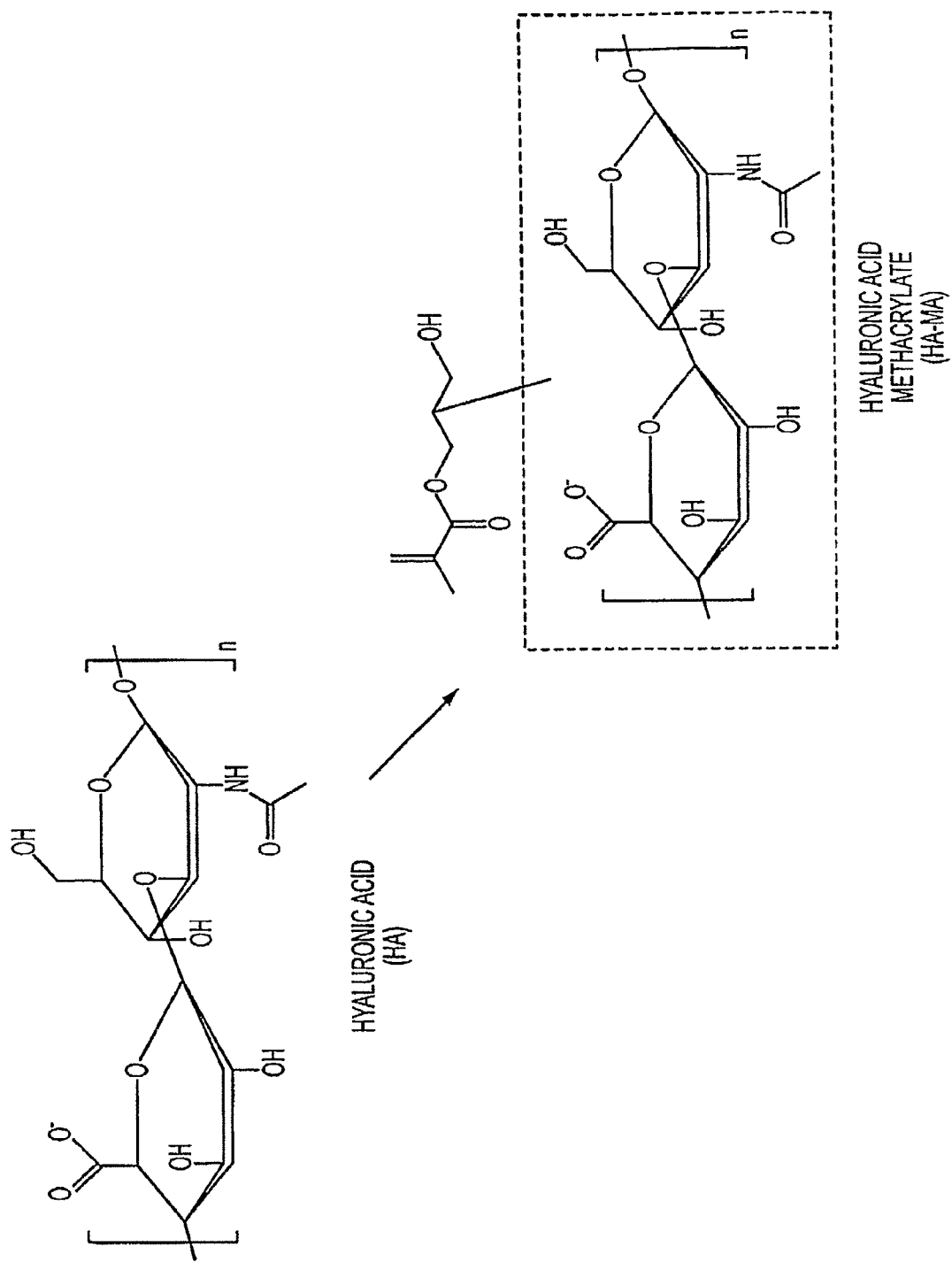
FIGS. 4A and 4B depict a synthetic scheme for derivatizing hyaluronic acid (HA) with GlcN.
Figure 4B:
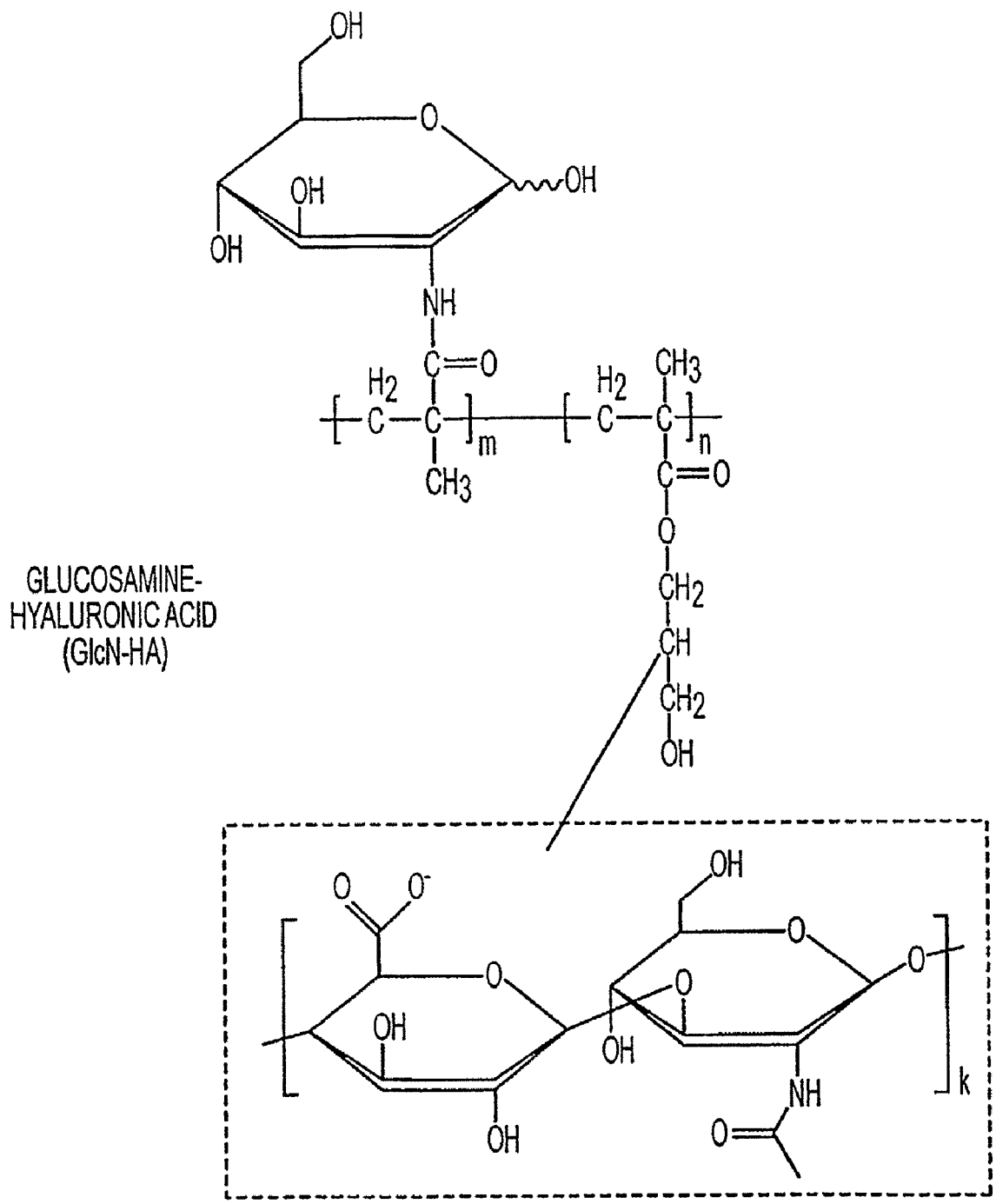

FIG. 3 depicts a synthetic scheme for derivatizing chondroitin sulfate (CS) with GlcN. CS is reacted with glycidyl methacrylate to yield chondroitin sulfate derivatized with a methacrylate group (CSMA). The methacrylate group can be found at any of three different reactive oxygen sites, one located at the carboxyl group, another at the 6' hydroxyl group, and the third on the sulfate group. The resulting chondroitin sulfate methacrylate can, for example, be reacted with, for example, the GlcN methacrylate provided hereinabove to yield chondroitin sulfate derivatized with GlcN.

Similarly, hyaluronic acid can be reacted with a methacrylate, such as glycidyl methacrylate, to yield hyaluronic acid methacrylate. The hyaluronic acid methacrylate then can be reacted with, for example, the GlcN methacrylate as described hereinabove to yield hyaluronic acid derivatized with GlcN.

A GlcN residue of interest can be derivatized with a number of different moieties to generate a reactive molecule suitable for polymerization or functionalization. Thus, GlcN is reacted with succinic anhydride in the presence of sodium bicarbonate and methanol to yield an N derivatized molecule (Kadokawa et al., J Macromol. Rapid Comm 15, 971, 1994). GlcN residues having different spacer lengths can be made using homologs of succinic anhydride or compounds related to succinic anhydride that contain structures that differ from the two carbon fragment found between the carboxyl functions found in succinic anhydride. The so derivatized GlcN molecules can be polymerized by reaction with hexachlorotriphosphazene in pyridine, as known in the art.

Some GlcNs of interest can be used as a lubricant, shock absorber or support mechanism. Thus, a GlcN of interest can be used as a replacement synovial fluid.

Other GlcNs of interest can be formed into films, such as available hyaluronic acid films which can be used to provide a temporary covering for or roof of a hole or void, such as a wound. The films also can be used as linings or coatings of devices, or prostheses and objects for implantation. The film can be affixed onto the device by mere adherence or the two opposing surfaces can be treated or derivatized with complementary reagents to ensure a bonding of the film to the surface.

In other embodiments, a GlcN of interest is configured to form a scaffold, grid, mesh or any form of a three-dimensional support, for example, to serve as a substitute for cell attachment in tissue engineering applications.

Such forms generally will be introduced surgically using known methods.

All references cited herein are incorporated by reference in entirety.

It should be understood that various changes and modifications to the presently preferred embodiments described herein will be apparent to those skilled in the art. Such changes and modifications can be made without departing from the spirit and scope of the present invention and without diminishing its intended advantages.

The invention is claimed as follows:

1. A composition comprising a biodegradable polymer comprising a plurality of glucosamine residues (GlcN), wherein the plurality of glucosamine residues are bound to biodegradable naturally occurring polysaccharide backbone.

2. The composition of claim 1, wherein said naturally occurring polysaccharide comprises chondroitin sulfate or hyaluronic acid.

* * * * *